(12) United States Patent
Lindström et al.

(10) Patent No.: US 12,409,082 B2
(45) Date of Patent: Sep. 9, 2025

(54) PANT-TYPE ABSORBENT ARTICLE

(71) Applicant: Essity Hygiene and Health Aktiebolag, Gothenburg (SE)

(72) Inventors: Åsa Lindström, Gothenburg (SE); Bert Deelen, Hoogezand (NL); Moa Olausson Wetterlund, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 374 days.

(21) Appl. No.: 17/919,624

(22) PCT Filed: May 14, 2020

(86) PCT No.: PCT/SE2020/050495
§ 371 (c)(1),
(2) Date: Oct. 18, 2022

(87) PCT Pub. No.: WO2021/230782
PCT Pub. Date: Nov. 18, 2021

(65) Prior Publication Data
US 2023/0149227 A1    May 18, 2023

(51) Int. Cl.
*A61F 13/535* (2006.01)
*A61F 13/53* (2006.01)
(Continued)

(52) U.S. Cl.
CPC .......... *A61F 13/535* (2013.01); *A61F 13/532* (2013.01); *A61F 2013/530737* (2013.01); *A61F 2013/53445* (2013.01)

(58) Field of Classification Search
CPC ............................. A61F 13/535; A61F 13/532
See application file for complete search history.

(56) References Cited

U.S. PATENT DOCUMENTS

| | | |
|---|---|---|
| 2006/0178650 A1 | 8/2006 | Hakansson et al. |
| 2012/0053545 A1 | 3/2012 | Love et al. |
| | (Continued) | |

FOREIGN PATENT DOCUMENTS

| | | |
|---|---|---|
| CL | 43780 B1 | 7/2002 |
| CL | 55183 B1 | 2/2009 |
| | (Continued) | |

OTHER PUBLICATIONS

Japanese Application No. 2022-568910; Office Action issued Jul. 18, 2024 with English translation; 6 pages.
(Continued)

*Primary Examiner* — Jessica Arble
(74) *Attorney, Agent, or Firm* — CANTOR COLBURN LLP

(57) ABSTRACT

Disclosed is an absorbent article including an absorbent member arranged between a topsheet and backsheet, the absorbent member having front edge and a rear edge, the absorbent member including a first layer having a first layer front edge and a first layer rear edge and a second layer, the first being shorter than the second layer, wherein the first and second layers include superabsorbent polymer particles, wherein the absorbent member is provided with at least two channels extending in a longitudinal direction and on a respective side of a longitudinal centerline of the absorbent article, the first layer including a higher amount of superabsorbent polymer particles than the second layer, the absorbent member having a total absorbent capacity of 1100 ml or more, wherein a ratio between the front edge distance and the rear edge distance is 1.5 or greater.

26 Claims, 8 Drawing Sheets

(51) Int. Cl.
  *A61F 13/532* (2006.01)
  *A61F 13/534* (2006.01)

(56) References Cited

U.S. PATENT DOCUMENTS

| | | | |
|---|---|---|---|
| 2013/0267924 A1 | 10/2013 | Mukai et al. | |
| 2014/0058348 A1* | 2/2014 | Arayama | A61F 13/4902 604/385.24 |
| 2014/0338822 A1 | 11/2014 | Mukai et al. | |
| 2015/0073373 A1 | 3/2015 | Mukai et al. | |
| 2015/0173968 A1 | 6/2015 | Joseph | |
| 2015/0173972 A1* | 6/2015 | Mukai | A61F 13/496 604/385.24 |
| 2015/0342796 A1 | 12/2015 | Bianchi et al. | |
| 2016/0206485 A1 | 7/2016 | Seitz et al. | |
| 2017/0156947 A1 | 6/2017 | Esquerra et al. | |
| 2017/0189246 A1 | 7/2017 | Yeoh | |
| 2017/0312148 A1* | 11/2017 | Dobrosielska-Oura | A61F 13/539 |
| 2018/0140477 A1 | 5/2018 | Minoguchi et al. | |
| 2019/0133844 A1* | 5/2019 | Mukai | A61F 13/51121 |
| 2019/0185112 A1 | 6/2019 | Patton | |

FOREIGN PATENT DOCUMENTS

| | | |
|---|---|---|
| CN | 103781447 A | 5/2014 |
| CN | 104958136 B | 5/2018 |
| CN | 108720999 A | 11/2018 |
| EP | 3357464 A1 | 7/2019 |
| JP | 2006043155 A | 2/2006 |
| JP | 2006141761 A | 6/2006 |
| JP | 2013046663 A | 3/2013 |
| JP | 2015519186 A | 7/2015 |
| JP | 2016104233 A | 6/2016 |
| JP | 2017064328 A | 4/2017 |
| JP | 2017217159 A | 12/2017 |
| JP | 2019170901 A | 10/2019 |
| JP | 6835532 B2 | 2/2021 |
| WO | 2009031592 A1 | 3/2009 |
| WO | 2019125298 A1 | 6/2019 |
| WO | 2019204973 A1 | 10/2019 |

OTHER PUBLICATIONS

International Search Report & Written Opinion for International Application No. PCT/SE2020/050495; International Filing Date: May 14, 2020; Date of Mailing: Jan. 13, 2021; 16 pages.
Notification of Transmittal of the International Preliminary Report on Patentability for International Application No. PCT/SE2020/050495; International Filing Date: May 14, 2020; Date of Mailing: Aug. 25, 2022; 7 pages.
Written Opinion of the International Preliminary Examining Authority for International Application No. PCT/SE2020/050495; International Filing Date: May 14, 2020; Date of Mailing: May 27, 2022; 6 pages.
Chinese Application No. 202080100133.X; Chinese Office Action with English Translation dated Jun. 29, 2024; 28 pages.
Chilean Application No. 2022-03151; Office Action issued Feb. 5, 2024 with English translation; 26 pages.
Japanese Application No. 2022-568910; Office Action issued Jan. 22, 2024 with English translation; 9 pages.
Colombian Application No. NC2022/0017105; Office Action dated Oct. 15, 2024; 7 pages.
Chinese Application No. 202080100133.X; Chinese Office Action with English Translation dated Feb. 17, 2023; 23 pages.
Chinese Application No. 202080100133.X; Chinese Office Action with English translation dated Aug. 18, 2023; 27 pages.

* cited by examiner

PANT-TYPE ABSORBENT ARTICLE

CROSS REFERENCE TO RELATED APPLICATIONS

This application is a National Stage application of PCT/SE2020/050495, filed May 14, 2020, which is incorporated by reference in its entirety herein.

TECHNICAL FIELD

The present disclosure pertains to a pant-type absorbent article such as a pant diaper, a sanitary pant or an incontinence pad. More specifically, the present disclosure pertains to a pant-type absorbent article adapted for use during nighttime or for bedridden users.

BACKGROUND

Disposable pant-type absorbent articles have defined core regions and elasticized front and rear regions to provide a comfortable fit and to enable the articles to be pulled up and down over the hips of the wearer. The pant-type articles are designed to allow the wearer or caregiver to easily put on and remove the article when it has been soiled. An absorbent core is disposed in the crotch portion of the absorbent article and is conventionally symmetrically disposed in respect to the rear and front regions.

Disposable pant-type absorbent articles used during nighttime needs to withstand relatively large amounts of liquid discharges and remain dry over a prolonged time. The wearer position and movement during nighttime differs from requirements of an absorbent article intended for daytime use.

It is an object for the present disclosure to provide a pant-type article intended for night-use or for bedridden users with improved comfort and reduced rewet and leakage.

SUMMARY

The above and other objects may be provided by a pant-type diaper according to claim 1. Further embodiments are set out in the dependent claims, in the following description and in the drawings.

A pant-type absorbent article such as a pant diaper, a sanitary pant or an incontinence pant according to the present disclosure comprises a chassis including a topsheet, a backsheet and an absorbent member arranged between the topsheet and the backsheet. The absorbent member has an absorbent member front edge and an absorbent member rear edge. The chassis comprises a front section, a rear section and a crotch section located between the front section and the rear section, as seen in a longitudinal direction of the absorbent article. The front section and the rear section are joined to each other along two opposite longitudinal side edges to define a waist-opening and a pair of leg-openings. The front section comprises front elastics and the rear section comprises rear elastics, each of the front elastics and the rear elastics extending between the respective opposite longitudinal side edges in a transverse direction of the absorbent article. The absorbent member comprises a first absorbent layer and a second absorbent layer. The first absorbent layer is arranged between the topsheet and the second absorbent layer. The first absorbent layer has a first absorbent layer front edge and a first absorbent layer rear edge. The second absorbent layer has a size and a shape in a plane of the absorbent article, the size and shape of the second absorbent layer defining the size and shape of the absorbent member in the plane of the absorbent article. The first absorbent layer is shorter than the second absorbent layer, as seen in the longitudinal direction, such that only the second absorbent layer is present in a front portion of the absorbent member, and in a rear portion of the absorbent member. The front elastics extend over the front portion of the absorbent member and the rear elastics extend over the rear portion of the absorbent member. The first absorbent layer front edge is arranged with a front edge distance from the absorbent member front edge and the first absorbent layer rear edge is arranged with a rear edge distance from the absorbent member rear edge. Each of the first and the second absorbent layer comprises superabsorbent polymer particles. The absorbent member is in a crotch portion thereof provided with at least two channels extending in the longitudinal direction and on a respective side of a longitudinal centerline of the absorbent article. The first absorbent layer comprises a higher amount of superabsorbent polymer particles than the second absorbent layer. The absorbent member may have a total absorbent capacity of 1100 ml or more, as measured according to standard test method ISO 11948-1. A ratio between the front edge distance and the rear edge distance is 1.5 or greater.

The term "absorbent article" refers to a product that is placed against the skin of the wearer to absorb and contain body exudates, like urine and faeces. The disclosure furthermore refers to a disposable absorbent articles, which means an article that is not intended to be laundered or otherwise restored or reused as an absorbent article after use. The disclosure refers to a "disposable pant-type absorbent article", having an outer cover being disposed on a garment facing side of the absorbent article and an absorbent core arranged in the crotch portion on a wearer facing side of the outer cover. Examples of such a pant-type absorbent article is a pant diaper, sanitary pant and incontinence pant. The absorbent article according to the present disclosure may be an adult incontinence article.

The present disclosure relates to absorbent articles intended for use during the night, or heavy-incontinence articles for bed-ridden users. It has been found that almost ⅓ of absorbent article leakages happens during the night. Caregivers need to wake up several times per night to check the absorbent article, interrupting the sleep of both themselves and the caretaker. Regularly disturbed sleeps may be a serious medical health risk. In the pant-type absorbent article according to the present disclosure, with the absorbent member having a total absorbent capacity of 1100 ml or more, the fact that the first absorbent layer comprises a higher amount of superabsorbent polymer particles than the second absorbent layer, has been seen to provide a dryer topsheet over a prolonged time providing the wearer with a dry feeling during night. This provides a better sleep to the user. Also, a dryer topsheet decreases the risk for skin irritations for the wearer.

As the first absorbent layer has been moved rearwards with respect to the absorbent member, the rear portion of the absorbent member is provided with a higher degree of absorbency to respond to the different absorbency need for a wearer lying down since most of the urine ends up being stored in the rear portion of the core. Wearing the same absorbent article during an entire night means a risk for over-hydration of the skin and skin irritations. The at least two channels provided in the absorbent member shapes the crotch portion of the absorbent article such that the liquid is guided to the central region of the crotch portion, as seen in the transverse direction, and rearwards where the absorbent article is provided with a high degree of absorbency.

The absorbent member may have a groin portion arranged between the front portion and the crotch portion and a buttocks portion arranged between crotch portion and the back portion, as seen in the longitudinal direction of the absorbent article. The first absorbent layer may layer extend from the groin portion and to the back portion of the absorbent member. The first absorbent layer may extend over groin portion, the crotch portion, the buttocks portion and to the transition between the buttocks portion and the back portion of the absorbent member. The first absorbent layer may be a shaped absorbent layer having a wider section, as seen in the transverse direction, arranged in the groin portion and a narrower section arranged in the crotch portion of the absorbent member.

The first absorbent layer may extend from the groin portion, such as from a transverse transition between the groin portion and the front portion of the absorbent member. The first absorbent layer may be wider in the frontmost part of the first absorbent layer, i.e. in the part arranged in the groin portion, and become more narrow in the crotch portion. Thereby the first absorbent layer conforms to the wearer anatomy and shapes the absorbent core to a bowl-shape in the groin portion since the thighs of the wearer will squeeze the wider part in the groin portion together and thereby guide the liquid to the crotch portion where absorbency capacity is available for storing of the liquid. Since the thighs of the wearer will also squeeze the crotch part together forming this section to a bowl-shape the liquid may also be temporarily stored there prior to being absorbed into the absorbent article.

The absorbent member may have a total length of from 250 mm, such as from 300 mm or from 400 mm. The absorbent member may have a total length of up to 1000 mm.

The length of the crotch portion may be from 20% to 25% of the length of the absorbent member and be arranged with equal distance to the absorbent member front edge and to the absorbent member rear edge.

The length of the buttocks portion may be from 25% to 35% of the length of the absorbent member.

The area of the buttocks portion may be at least 35% of the total area of the absorbent member. The area of the buttocks portion may be from 35% to 45% of the total area of the absorbent member.

The transition between the buttocks portion and the rear portion may correspond to the first absorbent layer rear edge.

The buttocks portion may thus be a larger and/or longer portion, thus providing additional protection in an absorbent article buttocks portion. This, in combination with the high total absorbency and the higher amount of superabsorbent particles in the upper, first absorbent layer has been found particularly advantageous for nighttime absorbent articles.

Optionally, 40% or more of the total absorbent capacity of the absorbent member may be provided in the buttocks portion.

The length of the groin portion may be from 15% to 25% of the length of the absorbent member. The transition between the front portion and the groin portion may correspond to the first absorbent layer front edge.

The first absorbent layer front edge may be arranged at level with the rearmost part of the front elastics, as seen in the longitudinal direction. At level with herein may correspond to a difference of +20 mm, such as ±10 mm, as seen in a longitudinal direction L. The front portion of the absorbent core is thus a single-core layer portion arranged under the front elastics providing the highly absorbent article with a less bulky front portion, tightly fitting against the belly of the wearer. This thus provides a comfortable, more aesthetically appealing night-product. However, the fact that the front portion fits tightly against the wearer also protects against side-front leakage.

The first absorbent layer rear edge may be arranged at level with the frontmost part of the rear elastics, as seen in the longitudinal direction. The rear portion of the absorbent core is thus a single-core layer portion arranged under the rear elastics providing the highly absorbent article with a flat rear portion, tightly fitting against the back of the wearer. The fact that the rear portion fits tightly against the back wearer provides extra protection against rear leakage. This also provides a comfortable, more aesthetically appealing night-product.

The ratio between the front edge distance and the rear edge distance may be 1.7 or greater, optionally up to 2.8.

A side elastic member may be arranged on each side of the absorbent member outside and along the crotch portion of the absorbent member. The side elastic member may for example be bands or strings of elastic material, e.g. foam elastics. The side elastic members may for example have a width of from 1 mm to 15 mm, such as 2 mm to 10 mm.

The absorbent article may comprise a transfer layer arranged between the topsheet and the first absorbent layer. The transfer layer may have a transfer layer front edge and a transfer layer rear edge. The transfer layer front edge may be arranged with a second front edge distance from the absorbent member front edge and the transfer layer rear edge being arranged with a second rear edge distance from the absorbent member rear edge. A ratio between the second front edge distance and the second rear edge distance may be 1 or greater.

Conventionally, transfer layers are arranged closer to the front edge than to the rear edge of the absorbent member. According to this aspect of the present disclosure, the transfer layer is centrally arranged or rearwards arranged with respect to a transverse centerline of the absorbent member. A transfer layer may be arranged between the topsheet and the absorbent member to receive and spread the liquid before it is absorbed by the absorbent member. As the liquid discharge for a night article, larger amounts of liquids may be received and contained in the absorbent structure. The fact that the transfer layer is arranged centrally or rearwards in the article with respect to the absorbent member ensures rapid inlet in the crotch and buttocks portion and has been found to, in combination with the specific core construction of the present disclosure, greatly reduce leakage during nighttime. When the user is lying down on their back when using the night-articles, some of the urine travels on the skin and hits the absorbent article more to the back area, with the wetting point thus being arranged from the crotch portion and to the buttocks and back portions. It is therefore important with rapid inlet in this area to prevent leakage in the back area.

The transfer layer may have a basis weight of 30 gsm or more, optionally of 40 gsm or more.

The transfer layer may for example be a nonwoven material, such as a spunbonded nonwoven material.

The amount in wt. % of superabsorbent polymer may be from 1.6 times higher in the first absorbent layer than in the second absorbent layer, preferably from 1.7 times higher in wt. % in the first absorbent layer than in the second absorbent layer. The amount in wt. % of superabsorbent polymer may be up to 4 times higher in wt. % in the first absorbent layer than in the second absorbent layer.

The first absorbent layer may comprise an amount of superabsorbent polymer particles of from 30 wt. % of the total first absorbent layer. The first absorbent layer may comprise an amount of superabsorbent polymer particles within the range of from 30 wt. % to 90 wt. % of the total first absorbent layer.

The second absorbent layer may comprise an amount of superabsorbent polymer particles of from 10 wt. % of the total second absorbent layer. Optionally an amount within the range of from 10 wt. % to 80 wt. % of the total second absorbent layer.

The two channels may be provided in the second absorbent layer. The two channels may be provided on a respective side of a longitudinal centerline of the absorbent article. The two channels may be provided outboard a respective longitudinal side edge of the first absorbent layer.

The area of the back portion of the absorbent member may be from 1.3 to 2.8 times greater than the area of the crotch portion of the absorbent member.

The groin portion may be free from the front elastics.

The absorbent article may comprise a crotch elastic member arranged on a garment facing side of the second absorbent layer, the crotch elastic member extending under the crotch portion of the absorbent member and along a longitudinal centerline of the pant-type absorbent article. The crotch elastic member may be a longitudinally extending elastic member, it may be in the form of elastic strings or an elastic band.

The pant-type absorbent article may comprise a third central channel being provided in the second absorbent layer, the third channel extending along the longitudinal centerline of the pant-type absorbent article and coinciding with the crotch elastic member.

The pant-type absorbent article may have a Rewet 3 value within the range of from 0 gsm to 5.5 gsm, as measured according to the Rewet Under Pressure method disclosed herein and after the $3^{rd}$ dose, The pant-type absorbent article may have a Rewet 4 value within the range of from 1 gsm to 12 gsm, such as 2 gsm to 11 gsm, as measured according to the Rewet Under Pressure method disclosed herein and after the $4^{th}$ dose.

The pant-type absorbent article may have a Rewet 5 value within the range of from 5 gsm to 23 gsm, as measured according to the Rewet Under Pressure method disclosed herein and after the $5^{th}$ dose.

The pant-type absorbent article may have a Rewet 6 value within the range of from 2 gsm to 13 gsm, as measured according to the Rewet Under Pressure method disclosed herein and 6 hours after the Rewet 5 measurement (about 7 hours after test start).

The pant-type absorbent article chassis comprises an elasticized waist portion, i.e. front elastics, such as comprising elastic members, such as elastic threads, contractably affixed between the outer cover garment facing nonwoven material and an further material layer provided on a wearer facing side of the nonwoven material. The chassis may also comprise an elastic laminate, such as for example elastic laminate comprising an elastic film which on opposite sides is bonded to first and second non-elastic fibrous nonwoven material. The laminate may be made by bonding the non-elastic fibrous nonwoven materials to the elastic film layer and subsequently stretching the composite material, causing the non-elastic materials to break. The elastic film material may be of a breathable material.

BRIEF DESCRIPTION OF THE DRAWINGS

The present disclosure will be further explained hereinafter by means of non-limiting examples and with reference to the appended drawings wherein.

DETAILED DESCRIPTION

It is to be understood that the drawings are schematic and that individual components, such as layers of materials are not necessarily drawn to scale. The pant-type absorbent article shown in the figures are provided as examples only and should not be considered limiting.

Figure 1:
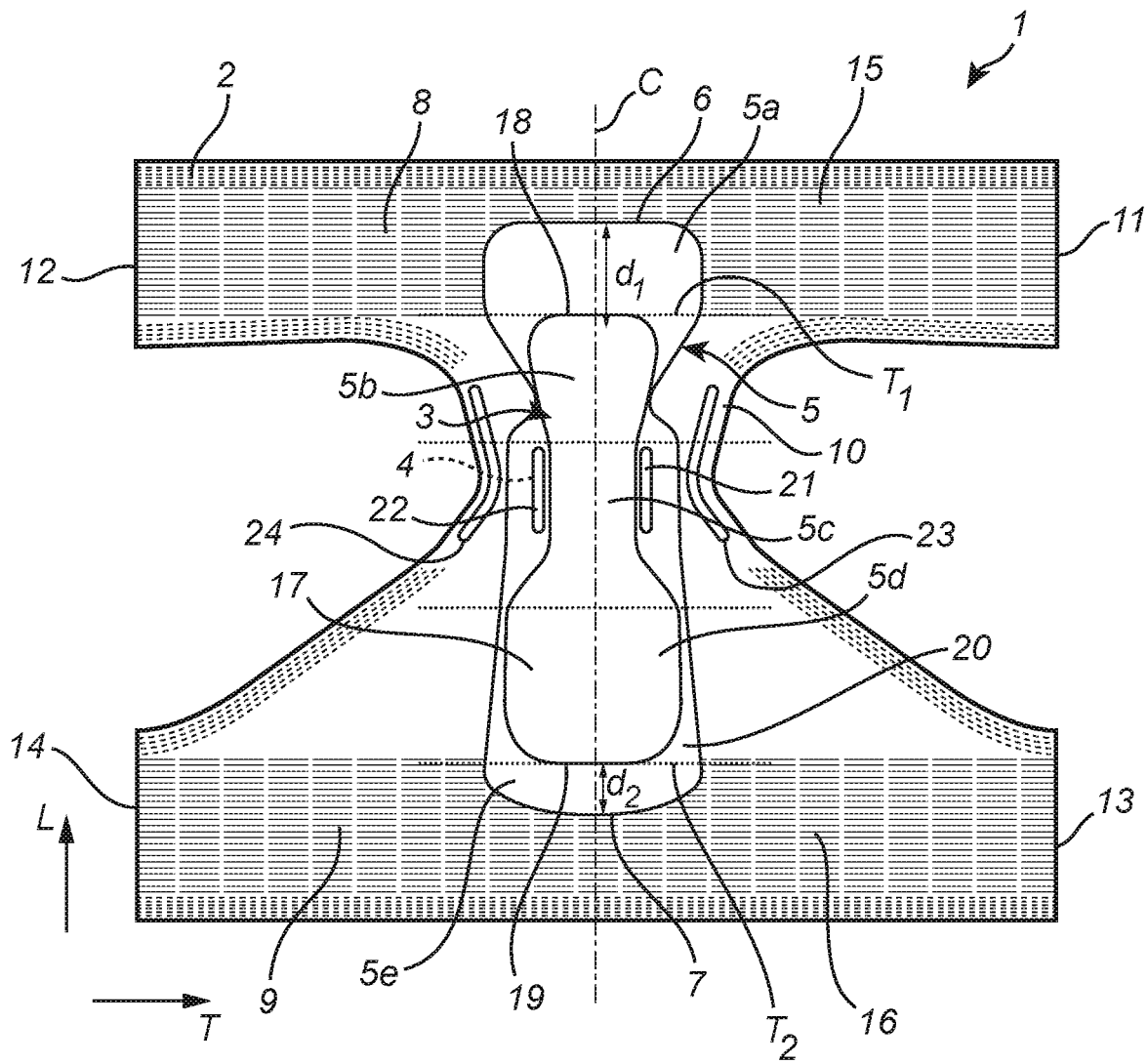
FIG. 1 illustrates a planar view of a pant-type absorbent article according to the present disclosure.

FIG. 1 is a planar view of a pant-type absorbent article 1 according to the present disclosure in the form of a pant diaper. The pant diaper 1 comprises a chassis 2 including a topsheet 3, a backsheet 4 and an absorbent member 5 arranged between the topsheet 3 and the backsheet 4. The absorbent member 5 has an absorbent member front edge 6 and an absorbent member rear edge 7. The chassis 2 comprises a front section 8, a rear section 9 and a crotch section 10 located between the front section 8 and the rear section 9, as seen in a longitudinal direction L of the pant diaper 1. The front section 8 and the rear section 9 are joined to each other along their respective opposite longitudinal side edges 11,12,13,14 to define a waist-opening and a pair of leg-openings (shown in FIG. 3). The front section 8 of the chassis 2 comprises front elastics 15 and the rear section 9 of the chassis 2 comprises rear elastics 16. Each of the front elastics 15 and the rear elastics 16 extend between the respective opposite longitudinal side edges 11,12,13,14 in a transverse direction T of the absorbent article 1, here in the form of elastic threads extending between the respective opposite longitudinal side edges 11,12,13,14 in a transverse direction T of the absorbent article 1. The absorbent member 5 comprises a first absorbent layer 17 having a first absorbent layer front edge 18 and a first absorbent layer rear edge 19 and a second absorbent layer 20. The second absorbent layer 20 has a size and a shape in a plane of the absorbent article 1, the size and shape of the second absorbent layer 20 defining the size and shape of the absorbent member 5 in the plane of the pant diaper 1. The first absorbent layer 17 is shorter than the second absorbent layer 20, as seen in the longitudinal direction L, such that only the second absorbent layer 20 is present in a front portion 5a of the absorbent member 5 and in a rear portion 5e of the absorbent member 5. The front elastics 15 extend over the front portion 5a of the absorbent member 5 and the rear elastics 16 extend over the rear portion 5e of the absorbent member 5, thereby forming a flat area in the front part and in the rear portion 5e of the absorbent member 5. The absorbent member 5 furthermore comprises a crotch portion 5c and a groin portion 5b arranged between the front portion 5a and the crotch portion 5c, a buttocks portion 5d is arranged between the rear portion 5e and the crotch portion 5c, as seen in the longitudinal direction L. The length of the crotch portion 5c is from 20% to 25% of the length of the absorbent member 5 and may be arranged with equal distance to the absorbent member front edge 6 and to the absorbent member rear edge 7, i.e. a transition between the groin portion 5b and the crotch portion 5a is arranged at and equal distance from the absorbent member front edge 6 as the distance of a transition between the crotch portion 5c and the buttocks portion 5d compared to the absorbent member rear edge 7. The length of the groin portion 5b is from 15% to 25% of the length of the absorbent member 5 and a transition T1 between the front portion 5a and the groin portion 5b corresponds to the first absorbent layer front edge 18. The transition T1 is furthermore arranged at level with the rearmost part of the front elastics 15, as seen in the longitudinal direction L and the groin portion 5b is thus free from the front elastics 15. At level with herein may correspond to a difference of +20 mm, such as ±10 mm, as seen in the longitudinal direction L.

The length of the buttocks portion 5d is from 25% to 35% of the length of the absorbent member 5 and the area of the buttocks portion 5d is 35% or more of the total area of the absorbent member 5. A transition T2 between the buttocks portion 5d and the rear portion 5e corresponds in this FIG. 1 to the first absorbent layer rear edge 19 and the transition T2 is arranged at level with the frontmost part of the rear elastics 16, as seen in the longitudinal direction L and the buttocks portion 5d is thus free from rear elastics 16. At level with herein may correspond to a difference of ±20 mm, such as ±10 mm, as seen in the longitudinal direction L.

The absorbent member 5 is provided with two channels 21,22 extending in the longitudinal direction L of the pant diaper 1 and on a respective side of a longitudinal centerline C of the pant diaper 1. In FIG. 1, the channels 21,22 are provided in the second absorbent layer 20 and outboard a respective longitudinal side edge of the first absorbent layer 17.

The first absorbent layer front edge 18 is arranged with a front edge distance d1 from the absorbent member front edge 6 and the first absorbent layer rear edge 19 is arranged with a rear edge distance d2 from the absorbent member rear edge 7. A ratio d1/d2 between the front edge distance d1 and the rear edge distance d2 is 1.5 or greater, optionally 1.7 or greater.

The absorbent core may comprise cellulosic fluff pulp and each of the first and the second absorbent layer 17,20 comprises superabsorbent polymer particles and the first absorbent layer 17 comprises a higher amount of superabsorbent polymer particles than the second absorbent layer 20. The absorbent member 5 has a total absorbent capacity of 1100 ml or more, as measured according to standard test method ISO 11948-1.

The liquid permeable topsheet 3 can be any suitable topsheet material as known by the person skilled in the art and may be fibrous topsheet material composed of a nonwoven material, e.g. spunbonded, meltblown, carded, hydroentangled, wetlaid etc.

Suitable nonwoven materials can be composed of natural fibers, such as woodpulp or cotton fibres, synthetic thermoplastic fibres, such as polyolefins, polyesters, polyamides and blends and combinations thereof or from a mixture of natural and synthetic fibres. Further examples of topsheet materials are porous foams. The materials suited as topsheet materials should be soft and non-irritating to the skin and be readily penetrated by body fluid, such as urine or menstrual fluid. The topsheet material may be essentially constituted of non-absorbent fibers, such as synthetic thermoplastic fibers, such as such as polyolefins, polyesters, polyamides and blends and combinations thereof. The synthetic fibers may be monocomponent fibers, bicomponent fibers or multicomponent fibers including polyesters, polyamides and/or polyolefins such as polypropylene and polyethylene.

The backsheet 4 may be any suitable backsheet material, such as a breathable or non-breathable plastic film. Examples of breathable materials are microporous polymeric films, nonwoven laminates from spunbond and meltblown layers, laminates from microporous polymeric films and nonwoven materials.

Figure 2:
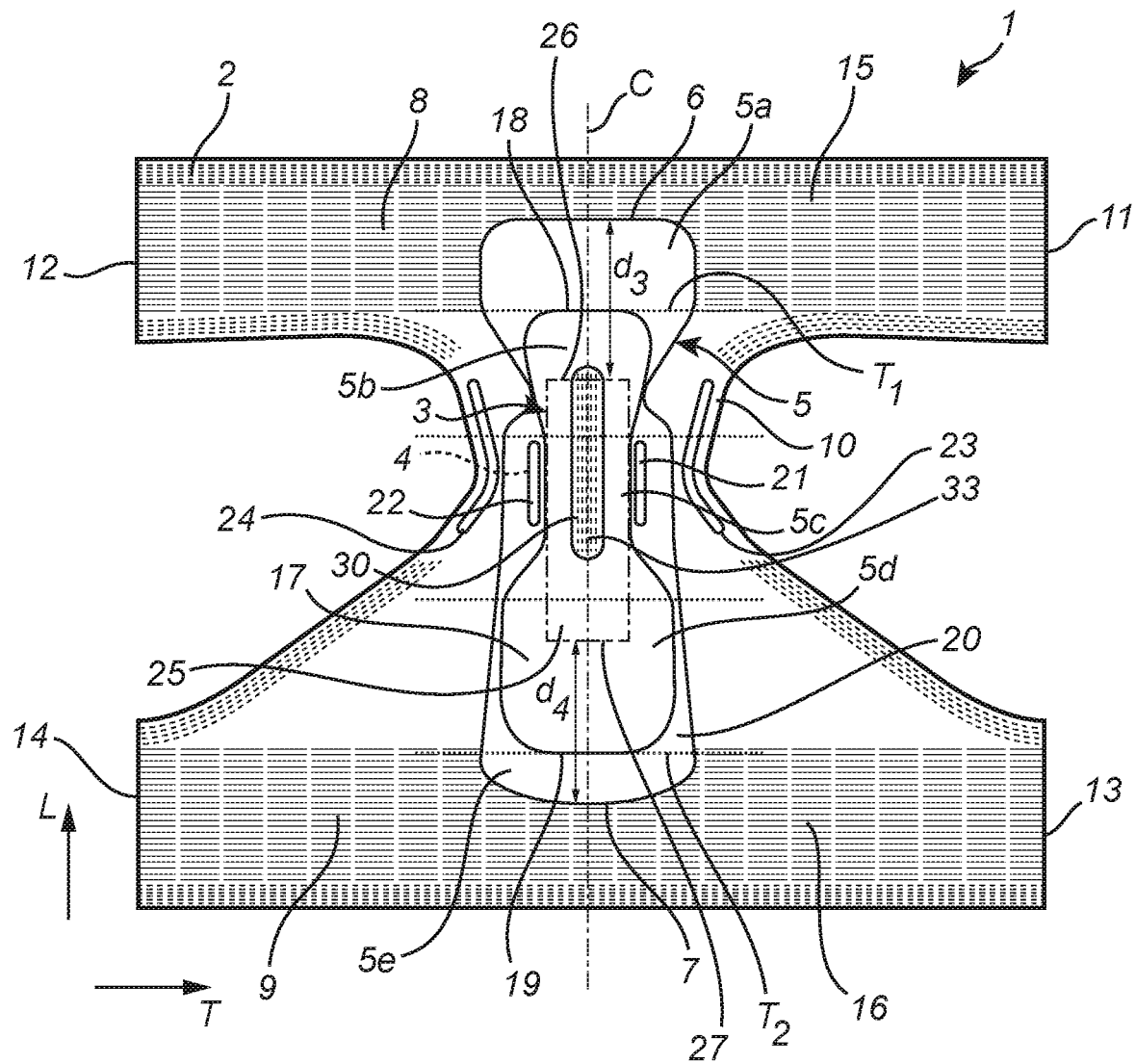
FIG. 2 illustrates a planar view of a pant-type absorbent article according to the present disclosure.

FIG. 2 illustrates a pant diaper 1 according to the present disclosure. The pant diaper 1 comprises a chassis 2 including a topsheet 3, a backsheet 4 and an absorbent member 5 arranged between the topsheet 3 and the backsheet 4. The absorbent member 5 has an absorbent member front edge 6 and an absorbent member rear edge 7. A transfer layer 25 is arranged between the topsheet 3 and the absorbent member 5. The absorbent member 5 comprises a front portion 5a, a rear portion 5e and a crotch portion 5c. A groin portion 5b is arranged between the front portion 5a and the crotch portion 5c and a buttocks portion 5d is arranged between the rear portion 5e and the crotch portion 5c, as seen in a longitudinal direction L of the pant diaper 1.

The absorbent member 5 comprises a first absorbent layer 17 and a second absorbent layer 20. The first absorbent layer 17 has a first absorbent layer front edge 18 and a first absorbent layer rear edge 19. The first absorbent layer 17 has a wider front and rear section and a narrower section in the crotch region. The wider front section of the first absorbent layer is arranged in the groin portion 5b of the absorbent member 5. The second absorbent layer 20 is wider than the first absorbent layer 17 except for in the groin portion 5b, where the first absorbent layer and the second absorbent layer 20 has essentially the same width.

The first absorbent layer 17 is shorter than the second absorbent layer 20, as seen in the longitudinal direction L, such that only the second absorbent layer 20 is present in the front portion 5a and the rear portion 5e of the absorbent member 5. The first absorbent layer 17 is an upper absorbent layer and arranged between the transfer layer 25 and the second absorbent layer 20. The transfer layer 25 has a transfer layer front edge 26 and a transfer layer rear edge 27. The transfer layer front edge 26 is arranged with a second front edge distance d3 from the absorbent member front edge 6 and the transfer layer rear edge 27 is arranged with a second rear edge distance d4 from the absorbent member rear edge 7. A ratio d3/d4 between the second front edge distance d3 and the second rear edge distance d4 is 1 or greater.

The chassis 2 comprises a front section 8, a rear section 9 and a crotch section 10 located between the front section 8 and the rear section 9, as seen in a longitudinal direction L of the pant diaper 1. The front section 8 and the rear section 9 are joined to each other along their respective opposite longitudinal side edges 11,12,13,14 to define a waist-opening and a pair of leg-openings. The front section 8 of the chassis 2 comprises front elastics 15 and the rear section 9 of the chassis 2 comprises rear elastics 16 and each of the front elastics 15 and the rear elastics 16 extend between the respective opposite longitudinal side edges 11,12,13,14 in a transverse direction T of the absorbent article 1. The front elastics 15 extend over the front portion 5a of the absorbent member 5 and the rear elastics 16 extend over the rear portion 5e of the absorbent member 5, thereby forming a flat area in the front part and in the rear portion of the absorbent member 5.

The second absorbent layer 20 is provided with two channels 21,22 extending in the longitudinal direction L of the pant diaper 1 and on a respective side of a longitudinal centerline C of the pant diaper 1. The second absorbent layer 20 also comprises a third central channel 33. The third central channel 33 extend in the crotch portion 5c of the absorbent member 5 in the longitudinal direction L of the pant diaper 1 and coincides with the longitudinal centerline C. The third central channel 33 furthermore extend partly in the groin portion 5b.

The chassis 2 of the pant diaper 1 illustrated in FIG. 2 comprises a crotch elastic member 30. The crotch elastic member 30 may be in the form of a plurality of parallel elastic strands or a piece of an elastic film. The crotch elastic member 30 extends under the crotch portion 5c of the absorbent member 5c and partly in the groin portion 5b along the longitudinal centerline C of the pant diaper 1. The third channel 33 coincides with the crotch elastic member 30.

Figure 3:
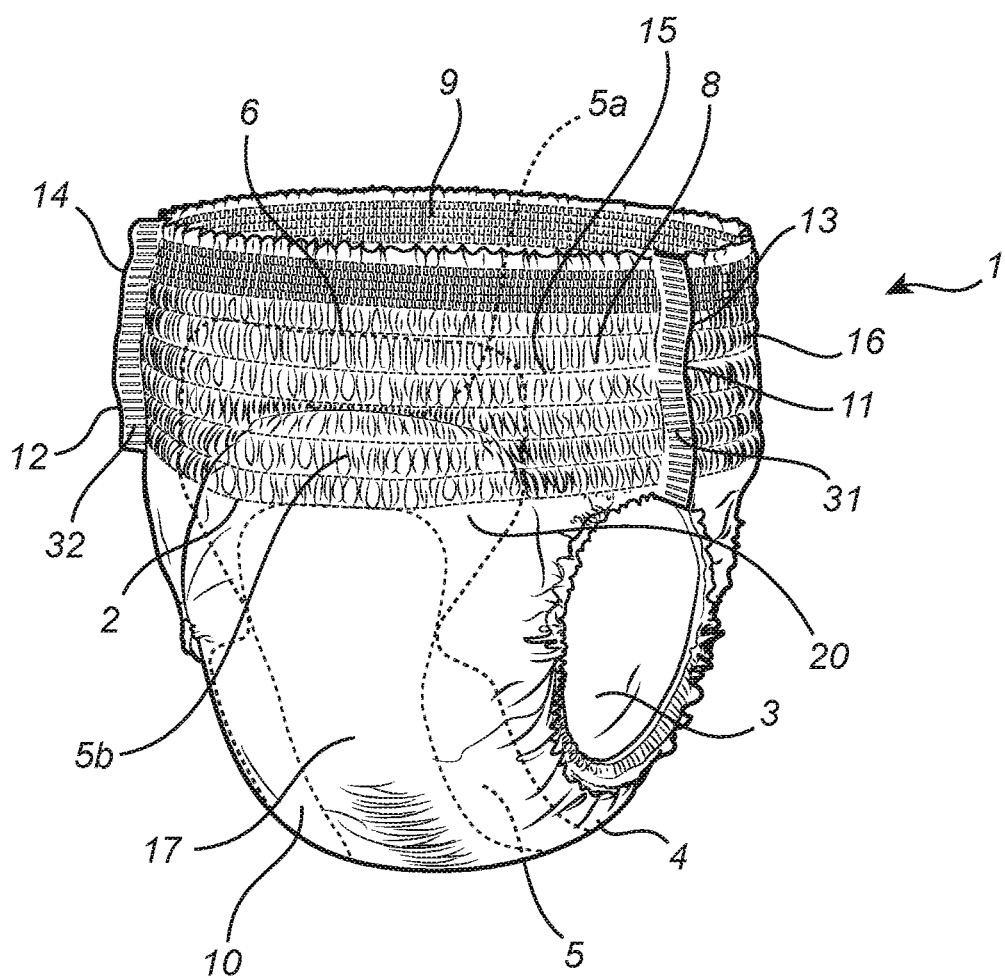
FIG. 3 is a perspective view of the pant-type absorbent article shown in FIG. 1 as assembled.

FIG. 3 illustrates the pant diaper from FIG. 1 in an assembled use-configuration. The pant diaper 1 includes the chassis 2, the topsheet 3, the backsheet 4 and the absorbent member 5 arranged between the topsheet 3 and the backsheet 4. The chassis 2 comprises the front section 8 provided with front elastics 15 in the form of elastic threads extending between the longitudinal front side edges 11,12 and the rear section 9 provided with rear elastics 16 in the form of elastic threads extending between the longitudinal rear side edges 13,14. The front and rear sections 8,9 are joined to each other at a first and a second side seams 31,32 to define a waist-opening and a pair of leg-openings. The front elastics 15 extend over the front portion 5a of the absorbent member 5 providing a flat portion at the belly of the wearer. The groin portion 5b of the absorbent member 5 having a decreasing width and the narrowest portion of the absorbent member 5 is arranged in the groin portion 5b.

Test Method—Rewet Under Pressure

The Rewet Under Pressure test method is a method for measuring rewet of a product after repeated wettings and under pressure, simulating the use-condition for a heavy-incontinence article after repeated wettings.

Equipment

Figure 4:
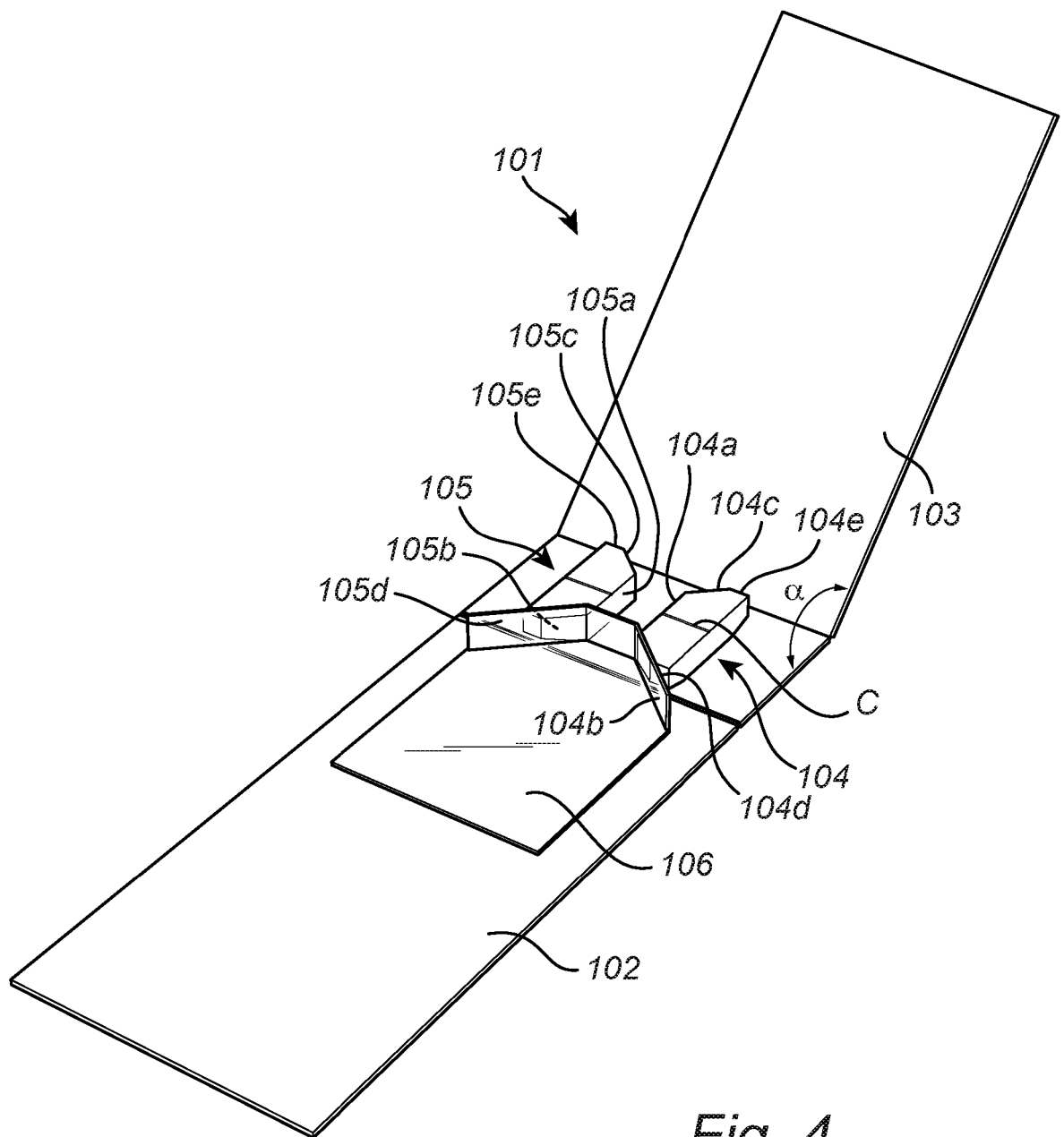
FIG. 4 shows a fixture for use in the Rewet under Pressure method as disclosed herein.
Figure 5A:
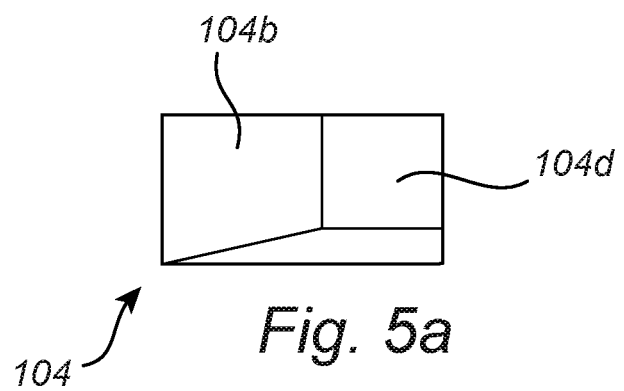
FIGS. 5a, 5b, and 5c show one of the two leg blocks for use in the Rewet under Pressure method as disclosed herein.
Figure 5B:
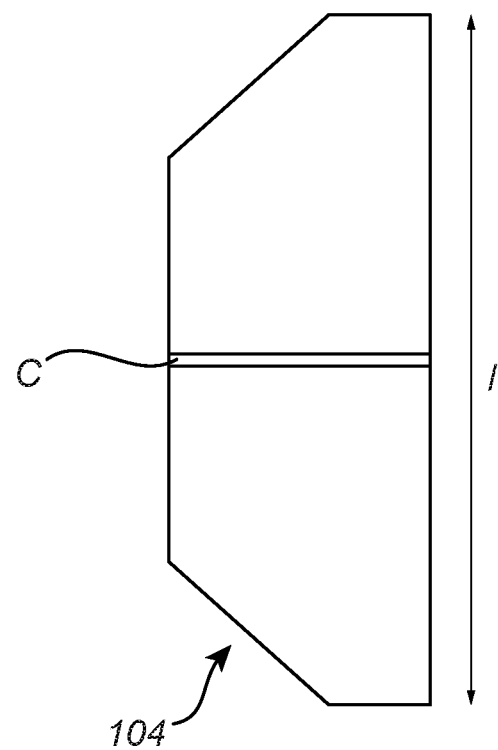
Figure 5C:
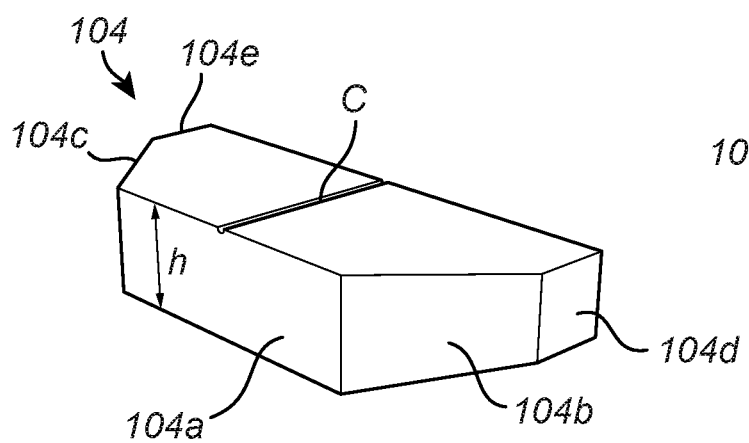
Figure 6A:
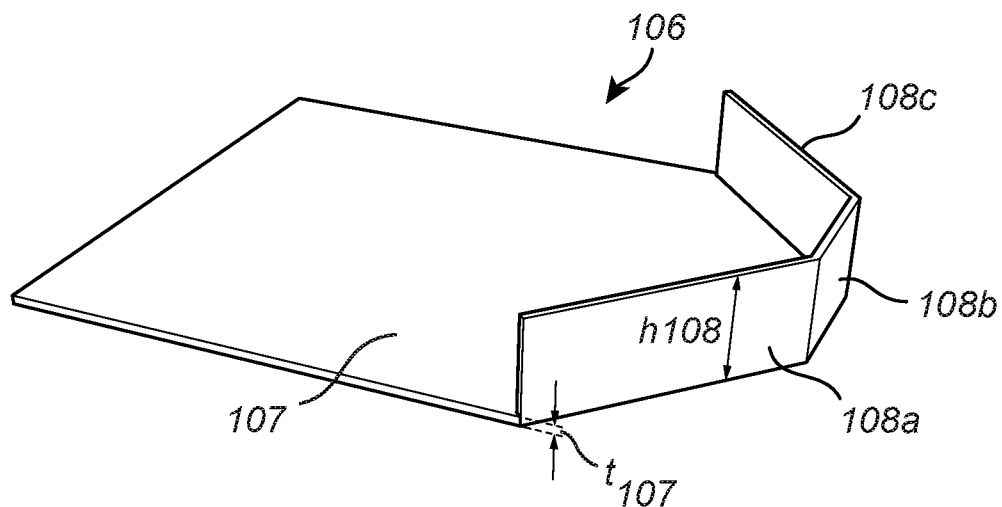
FIGS. 6a-6b show the buttocks template for use in the Rewet under Pressure method as disclosed herein.
Figure 6B:
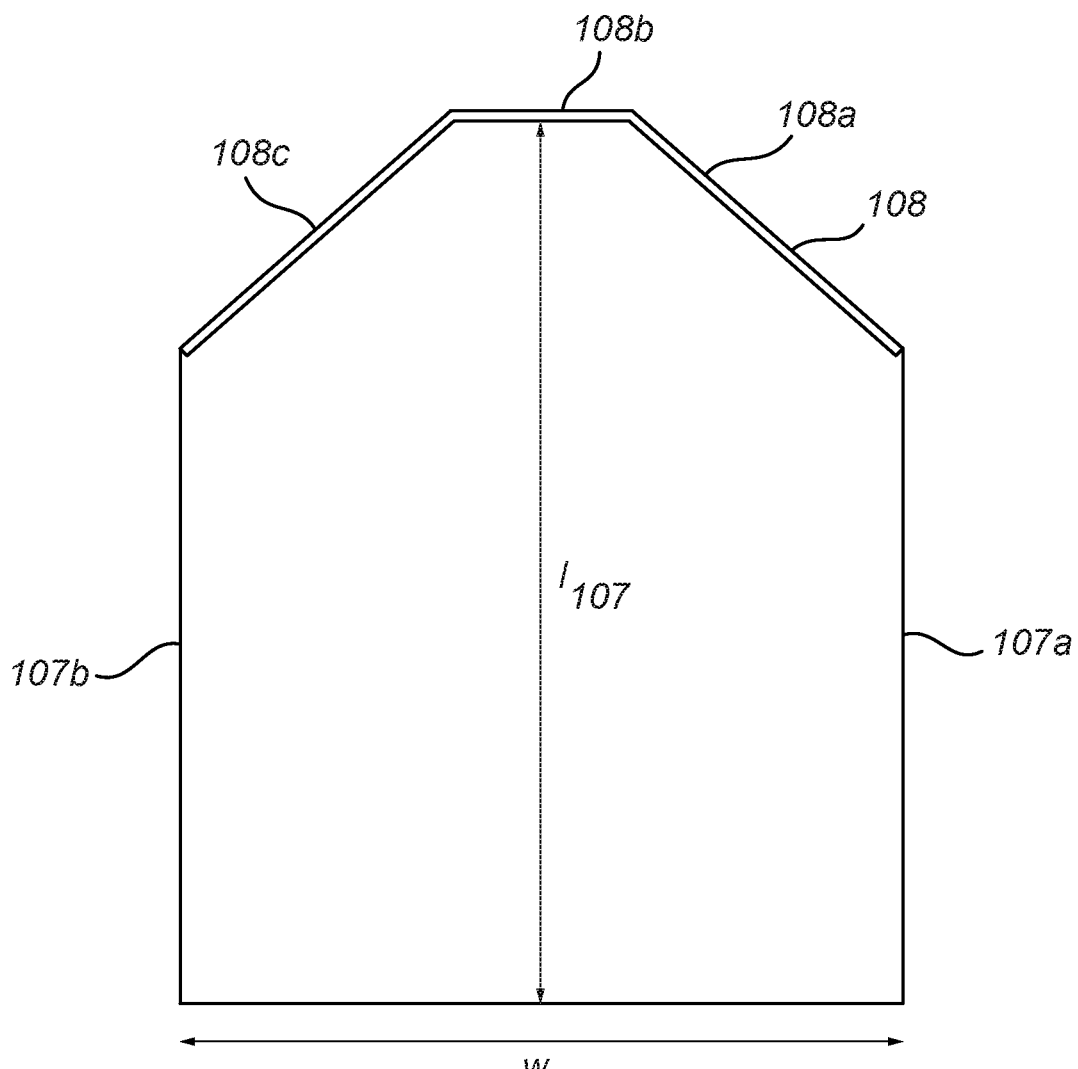

1. Fixture 101 made of polished aluminum (shown in FIG. 4). The fixture 101 comprises a first plate 102 measuring 200×420 mm, and a second plate 103 measuring 200×300 mm. The second plate 103 is arranged with an angle α of 60° with respect to the first plate 102.
2. Two leg blocks 104,105, made of hard plastic material (see FIGS. 4 and 5a-5c). The leg blocks 104, 105 each has a height h of 35 mm, as measured at its highest height, and length l of 120 mm, as measured at the longest length of the respective leg blocks 104,105. The width of the respective leg blocks 104,105, as taken along a center line C is 45 mm. The leg blocks 104,105 each comprise a respective inner vertical rectangular side 104a, 105a, each measuring 35×55 mm and being arranged to push against the longitudinal sides of a diaper when being arranged in the fixture 101. On a respective side of the inner rectangular sides 104a, 105a, the leg blocks 104,105 have respective block first side walls 104b, 105b and block second side walls 104c,105c. The block side walls 104b,105b,104c,105c are angled upwards and inwards and are arranged between the respective inner rectangular sides 104a, 105a and a respective first and second rectangular side wall 104d, 104e, 105d, 105e, each having a dimension of 20×20 mm. The second rectangular side walls 104e, 105e of the side blocks 104,105 are vertically aligned with a junction between the first and second plates 102, 103. The leg blocks 104, 105 are moveable in the cross direction of the fixture 101, and can be locked in position e.g. via screws or magnets.
3. Distance template (not shown), a rectangular steel block measuring 40×80 mm, with a height of about 20 mm.
4. Buttocks template 106 made of PMMA (Poly(methyl methacrylate)) or similar (shown in FIG. 4 and FIGS. 6a-6b), having a bottom plate 107 with a length $l_{107}$ of 175 mm, a width $w_{107}$ of 150 mm and a thickness $t_{107}$ of 6 mm. The buttocks template 106 has a template wall 108 having a height $h_{108}$ of 45 mm. The template wall 108 has three wall sections 108a, 108b, 108c, with a first side wall section 108a, a front wall section 108b and a second side wall section 108c. The front wall section 108b has a width of 50 mm and a height of 45 mm. The longitudinal sides 107a, 107b of the bottom plate 107 each has a length of 115 mm, as measured from a rear end edge of the bottom plate 107 to the respective side wall sections 108a,108c.
5. Metal weight 109, 10 kg.
6. Liquid pump 111 (shown in FIG. 8b), capable of a delivery rate of 10 ml/sec. The pump 111 is connected to a tube 112 with an internal diameter of 3 mm
7. Collagen film, available from Viscofan, Spain. The film is designated Coffi (transparent, article number 706). The film should be stored in a refrigerator, wrapped in plastic. For the rewet measurement, eight sheets are stacked, and cut or punched to dimensions 70×80 mm. The pad (of eight sheets) is suitably held together with a small staple. The pads are then placed in an enclosable polyethylene pouch before testing. Collagen film should be handled with tweezers.
8. Test fluid, 0.9% NaCl solution Procedure The evaluation is made in a stable laboratory environment set to 23° C. and 50% relative humidity. The absorbent articles are conditioned in this same environment for 24 hours before testing. At least six identical absorbent articles are tested. The procedure is described for one of these absorbent articles.

Figure 7:
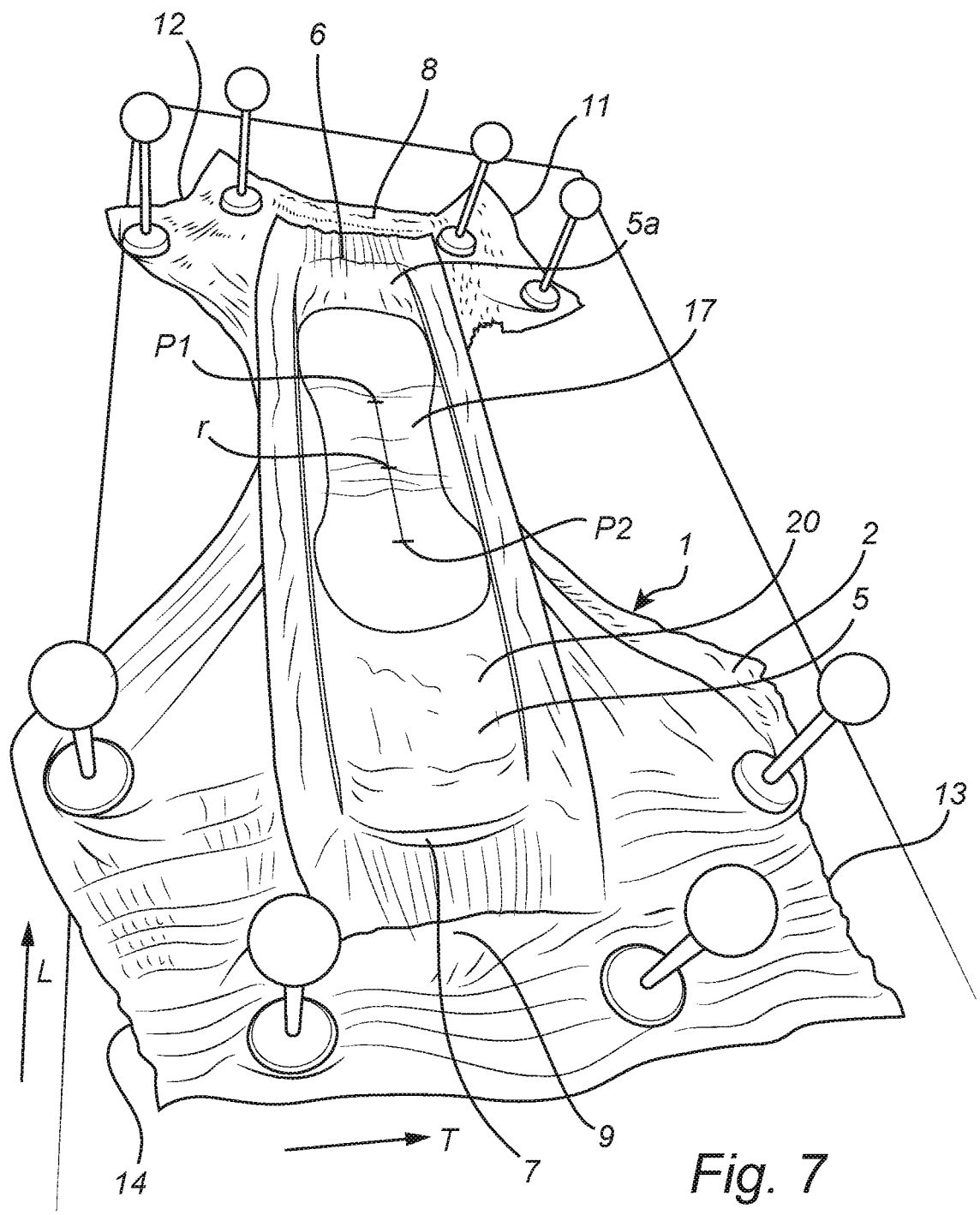
FIG. 7 shows a stretched absorbent article having been cut along the side seams and marked prior to testing in the Rewet under Pressure method as disclosed herein.

The absorbent article 1 to be tested is cut along the side seams to remove elastics, and stretched flat on a laboratory bench, as illustrated in FIG. 7. The front and rear sections 8,9 of the absorbent article 1 are marked (the front part faces the stomach of the user). The front edge 6 of the absorbent member 5 is identified. Based on the total length of the absorbent member 5 (100%), a crosswise reference line r is drawn over the topsheet of the absorbent article at a distance of 40% of the total length of the absorbent member from the front edge of the absorbent member 6. Mark a first inlet point P1 for liquid addition 70 mm forward from the reference line r (centered in a transverse direction direction T of the absorbent article 1). Mark a second point P2 65 mm rearward from the reference line r (centered in the transverse direction T), as a guide for placement of the collagen pad for the rewet measurement.

Figure 8A:
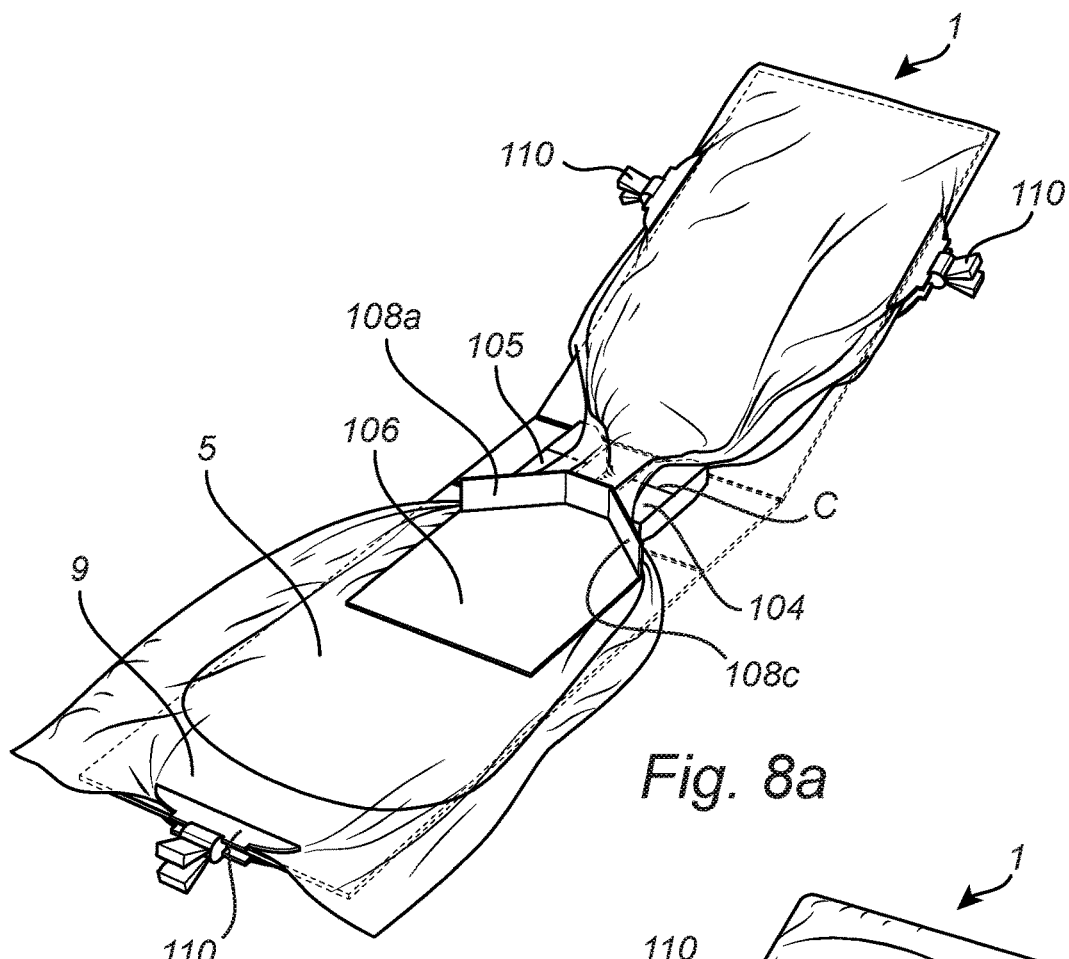
FIGS. 8a-8b show the absorbent article tested in the Rewet under Pressure method as disclosed herein.
Figure 8B:
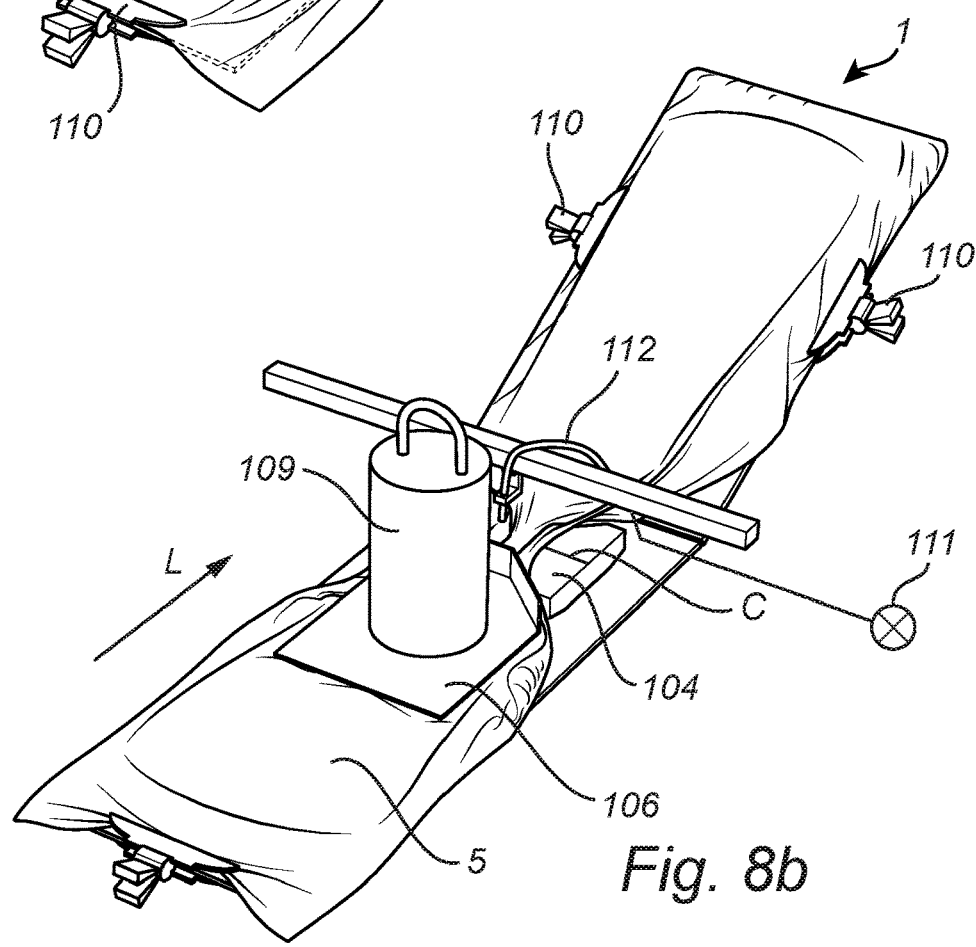

Place the 40×80 mm distance template centered onto the reference line r of the absorbent member 5 (the template length direction coincides with the longitudinal direction L of the absorbent article). Raise any longitudinal leakage barriers outside of the distance template, and slightly fold the longitudinal sides of the absorbent member 5 upwards (if there are no leakage barriers, raise the longitudinal edges of the absorbent member upwards along the sides of the distance template). Push the leg blocks 104,105 arranged on the first plate 102 outwards, to make space, and place the absorbent article 1 in the fixture 101, with the front section 8 of the absorbent article 1 resting on the second plate 103 as illustrated in FIG. 8a, with the buttocks template 106 removed from the fixture 101. Align the reference line r with the center line C of the respective leg blocks 104,105. Then push the leg blocks 104,105 against the distance template, and lock the blocks 104,105 in this position. Carefully stretch the front section 8 and rear section 9 of the absorbent article 1, to remove folds and irregularities (ensure that the alignment between the leg blocks is not affected). Fixate the absorbent article 1 against the first and second plates 2,3 with clamps 110 as illustrated in FIGS. 8a and 8b. Place the buttocks template 106 on the rearpart of the absorbent member 5, and push it forwards to align it against the leg blocks 104,105. The vertical wall sections 108a,108c having an angle inwardly towards the middle wall section 108b and are designed to fit tightly against the respective block first side walls 104b, 105b of the leg blocks 104,105. Remove the distance template. Place a 10 kg metal weight 109 centered onto the buttocks template 106 as illustrated in FIG. 8b. Arrange the fluid outlet tube 112 connected to the liquid pump 111 above the liquid inlet point, i.e. at a 90° angle to the plane of the absorbent article 1. The fluid outlet tube being arranged 10 mm above the liquid inlet point P1.

A total of five 100 ml doses are then added to the absorbent article 1. A stop watch is started when each dose has been absorbed (i.e. when there is no more pooled fluid on the diaper surface), and the subsequent dose is introduced after a waiting time of 15 minutes.

Rewet is measured 10 minutes after the third, fourth and fifth doses. For this purpose, remove the 10 kg weight and the buttocks template 12. Wipe the bottom side of the buttocks template 106, intended to be facing the absorbent article 1, free from liquid and moist. Weigh a collagen pad (8 sheets), and then place it on the absorbent article 1, with the length direction of the pad aligned with the longitudinal direction L of the absorbent article 1. The collagen pad is arranged by aligning the front edge of the collagen pad with the second point arranged 65 mm rearwards from the reference line r. The length of the collagen pad is positioned away from the reference line r, towards the rear part of the diaper. Then put the buttocks template back 106 over the collagen film and carefully lower the 10 kg weight onto the center of the buttocks template 106. After 30 seconds the weight and the buttocks template 106 are removed, the collagen pad is weighed, and liquid pick up is determined (wet collagen weight minus dry collagen weight). The buttocks template 106 and 10 kg weight are then put back, and the dosing schedule continues. A Rewet 3 value is measured after the third dose, a Rewet 4 value is measured after the fourth dose and a Rewet 5 is measured after the fifth dose. After the fifth dose the absorbent article 1 was let in the fixture 101 and under the pressure of the 10 kg weight for 6 hours and a Rewet 6 value was measured after 6 hours. The results are recalculated from grams to grams per square meter (gsm) with respect to the area of the collagen pad.

The total procedure takes about 7.5 hours corresponding to a night's sleep.

Comparative Tests

Comparative tests between an Example absorbent article and a Reference absorbent articles were carried out to compare the dryness of the topsheet under pressure, i.e. the rewet under pressure as measured according to the Rewet Under Pressure method disclosed herein.

Table 1 below illustrates the amount of absorbent materials in the first and second absorbent layers of the Example and the Reference article.

The reference article currently on the market is Tena Pant Super from Essity Hygiene and Health AB. The Example absorbent article and the reference article have the same Rothwell, total capacity, value of 2010 ml. Both of the articles comprises an absorbent member having a first absorbent layer, a second absorbent layer and a transfer layer arranged between the upper first absorbent layer and the topsheet. The dimension of the respective layer are substantially the same between the Example and the Reference article. In the Example absorbent article, the transfer layer is arranged 60 mm towards a rear edge of the absorbent member compared to the Reference article. For the Example absorbent article the first absorbent layer is arranged 25 mm more towards the ear edge of the absorbent member compared to the Reference article.

TABLE 1

|  |  | Fluff pulp (grams) | SAP (grams) |
|---|---|---|---|
| Example | First absorbent layer | 17.0 | 15.3 |
|  | Second absorbent layer | 22.5 | 8.0 |
| Ref. article | First absorbent layer | 14.3 | 9.7 |
|  | Second absorbent layer | 21.4 | 15.2 |

Table 2, shown below, shows test data from an Example absorbent article according to the present disclose compared with the Reference absorbent article currently on the market.

TABLE 2

| Absorbent article | No. of replicates | Rewet 3 (gsm) | Rewet 4 (gsm) | Rewet 5 (gsm) | Rewet 6 (gsm) |
|---|---|---|---|---|---|
| Example | 15 | 3.8 | 9.9 | 21.3 | 9.5 |
| Ref. article | 9 | 6.9 | 14.0 | 24.3 | 14.0 |

As may be seen from Table 2, the rewet values are significantly lower for the Example absorbent article, demonstrating the dryer topsheet of the Example absorbent article, both after repeated wettings and over a prolonged period of time.

The invention claimed is:

1. A pant-type absorbent article defining a longitudinal direction and a transverse direction orthogonal to the longitudinal direction, the absorbent article comprising:
   a chassis;
   a topsheet;
   a backsheet; and
   an absorbent member arranged between the topsheet and the backsheet,
   wherein the absorbent member has an absorbent member front edge and an absorbent member rear edge,
   wherein the chassis comprises a front section, a rear section and a crotch section located between the front section and the rear section, as seen in the longitudinal direction of the absorbent article,
   wherein the front section and the rear section are joined to each other along respective opposite longitudinal side edges thereof to define a waist-opening and a pair of leg-openings,
   wherein the front section comprises front elastics and the rear section comprises rear elastics, wherein each of the front elastics and the rear elastics extend between the respective opposite longitudinal side edges in the transverse direction (T) of the absorbent article, wherein the absorbent member comprises a first absorbent layer and a second absorbent layer, wherein the first absorbent layer is arranged between the topsheet and the second absorbent layer, wherein the first absorbent layer has a first absorbent layer front edge and a first absorbent layer rear edge, wherein the second absorbent layer has a size and a shape in a plane of the absorbent article that define the size and shape of the absorbent member in the plane of the absorbent article, wherein the first absorbent layer is shorter than the second absorbent layer, as seen in the longitudinal direction, such that only the second absorbent layer is present in a front portion and a rear portion of the absorbent member, wherein the front elastics extend over the front portion of the absorbent member and the rear elastics extend over the rear portion of the absorbent member, wherein the first absorbent layer front edge is arranged with a front edge distance (d1) from the absorbent member front edge and the first absorbent layer rear edge is arranged with a rear edge distance (d2) from the absorbent member rear edge, wherein each of the first and the second absorbent layer comprises superabsorbent polymer particles, wherein the absorbent member in a crotch portion thereof is provided with at least two channels extending in the longitudinal direction and on a respective side of a longitudinal centerline of the absorbent article, wherein the first absorbent layer comprises a higher amount of superabsorbent polymer particles than the second absorbent layer, the absorbent member having a total absorbent capacity of 1100 ml or more, as measured according to standard test method ISO 11948-1, and wherein a ratio between the front edge distance (d1) and the rear edge distance (d2) is 1.5 or greater.

2. The pant-type absorbent article according to claim 1, wherein the absorbent member has a groin portion arranged between the front portion and the crotch portion and a buttocks portion arranged between crotch portion and the back portion, as seen in the longitudinal direction of the absorbent article, wherein the first absorbent layer extends from the groin portion and to the back portion of the absorbent member, and wherein the first absorbent layer is a shaped absorbent layer having a wider section, as seen in the transverse direction, arranged in the groin portion and a narrower section arranged in the crotch portion of the absorbent member.

3. The pant-type absorbent article according to claim 1, wherein the length of the crotch portion is from 20% to 25% of the length of the absorbent member and is arranged with equal distance to the absorbent member front edge and to the absorbent member rear edge.

4. The pant-type absorbent article according to claim 1, wherein the length of the buttocks portion is from 25% to 35% of the length of the absorbent member.

5. The pant-type absorbent article according to claim 1, wherein a transition between the buttocks portion and the rear portion corresponds to the first absorbent rear edge.

6. The pant-type absorbent article according to claim 1, wherein the area of the buttocks portion is at least 35% of the total area of the absorbent member.

7. The pant-type absorbent article according to claim 1, wherein the 40% or more of the total absorbent capacity of the absorbent member is provided in the buttocks portion.

8. The pant-type absorbent article according to claim 1, wherein the length of the groin portion is from 15% to 25% of the length of the absorbent member.

9. The pant-type absorbent article according to claim 1, wherein a transition between the front portion and the groin portion corresponds to the first absorbent layer front edge.

10. The pant-type absorbent article according to claim 1, wherein the first absorbent layer front edge is posited to be level with the rearmost part of the front elastics, as seen in the longitudinal direction.

11. The pant-type absorbent article according to claim 1, wherein the ratio between the front edge distance (d1) and the rear edge distance (d2) is 1.7 or greater.

12. The pant-type absorbent article according to claim 1, a side elastic member is arranged on each side of the absorbent member outside and along the crotch portion of the absorbent member.

13. The pant-type absorbent article according to claim 1, wherein the absorbent article comprises a transfer layer arranged between the topsheet and the first absorbent layer, wherein the transfer layer has a transfer layer front edge and a transfer layer rear edge, wherein the transfer layer front edge is arranged with a second front edge distance from the absorbent member front edge, wherein the transfer layer rear edge is arranged with a second rear edge distance from the absorbent member rear edge, and wherein a ratio between the second front edge distance and the second rear edge distance is 1 or greater.

14. The pant-type absorbent article according to claim 13, wherein the transfer layer has a basis weight of 30 gsm or more.

15. The pant-type absorbent article according to claim 1, wherein the amount in wt. % of superabsorbent polymer is at least 1.6 times higher in the first absorbent layer than in the second absorbent layer.

16. The pant-type absorbent article according to claim 1, wherein the first absorbent layer comprises an amount of superabsorbent polymer particles of at least 30 wt. % of the total first absorbent layer.

17. The pant-type absorbent article according to claim 1, wherein the second absorbent layer comprises an amount of superabsorbent polymer particles of at least 10 wt. % of the total second absorbent layer.

18. The pant-type absorbent article according to claim 1, wherein the two longitudinally extending channels are provided in the second absorbent layer.

19. The pant-type absorbent article according to claim 1, wherein an area of the back portion of the absorbent member is from 1.3 to 2.8 times greater than an area of the crotch portion of the absorbent member.

20. The pant-type absorbent article according to claim 1, wherein the groin portion is free from the front elastics.

21. The pant-type absorbent article according to claim 1, wherein the absorbent article comprises a crotch elastic member arranged on a garment facing side of the second absorbent layer, the crotch elastic member extending under the crotch portion of the absorbent member and along a longitudinal centerline of the pant-type absorbent article.

22. The pant-type absorbent article according to claim 21, wherein a third central channel is provided in the second absorbent layer, the third channel extending along the longitudinal centerline of the pant-type absorbent article and coinciding with the crotch elastic member.

23. The pant-type absorbent article according to claim 1, wherein the absorbent article has a Rewet 3 value within the range of from 0 gsm to 5.5 gsm.

24. The pant-type absorbent article according to claim 1, wherein the absorbent article has a Rewet 4 value within the range of from 1 gsm to 12 gsm.

25. The pant-type absorbent article according to claim 1, wherein the absorbent article has a Rewet 5 value within the range of from 5 gsm to 23 gsm.

26. The pant-type absorbent article according to claim 1, wherein the absorbent article has a Rewet 6 value within the range of from 2 gsm to 13 gsm.

* * * * *